United States Patent [19]

Tashiro et al.

[11] Patent Number: 4,542,236

[45] Date of Patent: Sep. 17, 1985

[54] PROCESS FOR PREPARING OPTICALLY ACTIVE PHENYLALANINE

[75] Inventors: Yasuhisa Tashiro, Yokohama; Shigeru Aoki, Matsudo, both of Japan

[73] Assignee: Nippon Kayaku Kabushiki Kaisha, Tokyo, Japan

[21] Appl. No.: 634,228

[22] Filed: Jul. 25, 1984

[30] Foreign Application Priority Data

Aug. 2, 1983 [JP] Japan ................................ 58-140591
Feb. 24, 1984 [JP] Japan ................................ 59-32543

[51] Int. Cl.$^4$ ........................................... C07B 19/00
[52] U.S. Cl. ..................................... 562/401; 562/443
[58] Field of Search ................................ 562/401, 443

[56] References Cited

U.S. PATENT DOCUMENTS 4,151,198 4/1979 Halmos ........................... 260/501.11
4,198,524 4/1980 Tashiro et al. .................. 562/401 X

OTHER PUBLICATIONS

Koga et al: "Asymmetric Interaction Between Mandelic Acid and Aromatic α-Amino Acids in Aqueous System." *Nippon Kagaku Zasshi*, 92(11), 999–1002, (1971) with translation.
*Chemical Abstracts*, vol. 77, 19976j, (1972).

*Primary Examiner*—Natalie Trousof
*Assistant Examiner*—Vera C. Clarke
*Attorney, Agent, or Firm*—Cushman, Darby & Cushman

[57] ABSTRACT

The present invention relates to a process for preparing optically active phenylalanine which comprises resolving mixture of a complex of D-phenylalanine and optically active mandelic acid and a complex of L-phenylalanine and optically active mandelic acid in a solvent containing hydrochloric acid, carboxylic acid, phosphoric acid or a salt thereof to obtain the complex having lower solubility, and removing said optically active mandelic acid from the obtained complex to obtain an optically active phenylalanine.

In the case of resolving DL-phenylalanine by the process according to the present invention, the amount of mother liquor used in resolution can be made to about ½ to 1/6 as compared to the amount of mother liquor of which the acidic compound or the salt thereof is not used in the resolution. Accordingly, the process according to the present invention is extremely profitable as an industrial process for producing an optically active phenylalanine.

10 Claims, No Drawings

PROCESS FOR PREPARING OPTICALLY ACTIVE PHENYLALANINE

BACKGROUND OF THE INVENTION

The present invention relates to a process for preparing optically active phenylalanine.

A process for resolving DL-phenylalanine with an optically active mandelic acid has been already known (refer to "NIPPON KAGAKU ZASSHI" 92(11) 999–1002 (1971)). However, according to the present inventors' tracing of the publicly known process, the complex of phenylalanine and mandelic acid has a extremely low solubility in water as low as 2.6% by weight (calculated as phenylalanine) and therefore, the solubility ratio of the obtained complex of an optically active phenylalanine and the optically active mandelic acid to the mother liquor used in the resolution is extremely low. So, the known process is extremely disadvantageous in industrial scale.

As a result of the present inventors' studies for improving the disadvantage of the publicly known process, it has been found that complexes of DL-phenylalanine and an optically active mandelic acid is resolved in a solvent containing hydrochloric acid, a carboxylic acid, phosphoric acid or a salt thereof without decomposing the complexes and in addition, it has been found that the amount of the mother liquor used in the resolution is ½ to 1/6 of the amount of the mother liquor according the the known process of which such an acid compound or a salt thereof is not used. The present invention has been accomplished by the present inventors based on the knowledges mentioned above.

SUMMARY OF THE INVENTION

It is an object of the present invention to provide a process for preparing optically active phenylalanine from the complex of phenylalanine and mandelic acid, which comprises resolving the mixture of a complex of D-phenylalanine and optically active mandelic acid and a complex of L-phenylalanine and optically active mandelic acid in a solvent containing hydrochloric acid, carboxylic acid, phosphoric acid or a salt thereof to obtain the complex having lower solubility, and removing said optically active mandelic acid from the obtained complex to obtain optically active phenylalanine.

Other objects and advantages of the present invention will be apparent hereinafter.

DETAILED DESCRIPTION OF THE INVENTION

As a carboxylic acid used in the process according to the present invention, aliphatic carboxylic acid such as lower fatty acid, lower aliphatic hydroxycarboxylic acid and lower aliphatic dicarboxylic acid are mentioned. As lower fatty acid, fatty acids having two to four carbon atoms are preferable. For example, saturated fatty acids such as acetic acid, propionic acid, butyric acid and the like, and unsaturated fatty acids such as acrylic acid, crotonic acid, vinylacetic acid and the likes may be mentioned. As lower aliphatic hydroxycarboxylic acid, those aliphatic hydroxycarboxylic acid having two to four carbon atoms are preferable. For example, lactic acid may be mentioned. As lower aliphatic dicarboxylic acid, aliphatic dicarboxylic acid having two to four carbon atoms are preferable. For example, saturated aliphatic dicarboxylic acid such as oxalic acid, malonic acid and the likes, and unsaturated aliphatic dicarboxylic acid such as maleic acid and the likes may be mentioned. As a salt thereof, a metallic salt such as sodium salt and potassium salt or ammonium salt may be mentioned. As a salt of phosphoric acid, sodium salt, potassium salt, ammonium salt and the like of phosphoric acid such as sodium dihydrogen phosphate, potassium dihydrogen phosphate and the likes may be mentioned.

As a solvent for use in the process according to the present invention, any solvent may be used provided that each of the above-mentioned acids, the salts thereof, phenylalanine and mandelic acid can dissolve in the solvent and a complex of phenylalanine and mandelic acid can be formed in the solvent. For instance, the carboxylic acid mentioned above may be used as a solvent in the case where carboxylic acid is a liquid at ordinary temperature. From industrial viewpoint, water is most preferable as a solvent.

The carboxylic acid or the salt thereof may be used at a concentration of higher than 20 w/w % and phosphoric acid or the salt thereof may be used at the concentration of 5 to 28 w/w % or 30 to 50 w/w %, respectively. Carboxylic acid, phosphoric acid or a salt thereof to be contained in a solvent is preferably used in the range of the concentration of which one of the two complexes of optically active phenylalanine (D-isomer or L-isomer) and optically active mandelic acid is easily dissolved in the solvent before resolution. Concretely, it is preferable to use a carboxylic acid or a salt thereof at a concentration of 40 to 90 w/w % and also, it is preferable to use phosphoric acid or a salt thereof at concentration of 10 to 25 w/w %.

In the case of hydrochloric acid, it is preferable that the amount of hydrochloric acid to be used is 2 parts by mole or less than 2 parts by mole to one parts by mole of DL-phenylalanine, more preferably about 0.2 to 1.6 parts by mole to one part by mole of the mixture of a complex of D-phenylalanine and optically active mandelic acid and a complex of L-phenylalanine and optically active mandelic acid, most preferably about 0.6 to 1.2 parts by mole to one part by mole of the mixture.

The process of the present invention can be carried out as follows.

For example, DL-phenylalanine and optically active mandelic acid (D-isomer or L-isomer) are dissolved in a solvent containing hydrochloric acid, carboxylic acid, phosphoric acid or a salt thereof to produce a complex of D-phenylalanine and optically active mandelic acid and a complex of L-phenylalanine and optically active mandelic acid. Afterwards, one of the complexes is separated by fractional crystallization in which the resultant solution is cooled or is optionally condensed to crystallize the complex having a lower solubility in the solvent. The separated crystals of the complex is collected by filtration. The collected complex of optically active phenylalanine and optically active mandelic acid is dissociated by a treatment with an ion-exchange resin or a neutralization to remove optically active mandelic acid and as a result, optically active phenylalanine is obtained. A racemizing agent may be added to the solvent at the time of resolution.

When a complex of optically active phenylalanine and optically active mandelic acid is produced, optically active mandelic acid is preferably used in an amount of more than 0.1 part by mole to one part by mole of DL-phenylalanine, more preferably 0.5 to 6 parts by mole to one part by mole of DL-phenylalanine, most preferably 1 to 3 parts by mole to one part by mole of DL-phenylalanine. In any case, the amount of optically acitve mandelic acid to be used is determined while considering the concentration or the amount of hydrochloric acid, carboxylic acid, phosphoric acid or a salt thereof contained in the solvent.

The complex according to the present invention is produced at a temperature higher than 0° C., preferably, at a temperature of 50° C. to the boiling point of the solvent used in resolution.

In general, the temperature of fractional crystallization is lower than the boiling point of the solvent used in resolution, preferably, 0° C. to 50° C.

The ordinary crystallization time is about 1 to 4 hours. Although it is not necessary to particularly add any seed crystals at the time of the crystallization, an addition of a minute amount of the seed crystals for accelerating the crystallization causes no inconvenience.

In the case where the obtained optically active complex is not pure, the pure complex can be easily obtained by recrystallization or the like as occasion arises.

The isolation of the optically active phenylalanine from the obtained complex can be carried out by the publicly known method. For instance, an aqueous solution containing the complex of an optically active phenylalanine and an optically active mandelic acid is neutralized by a caustic alkali, the optically active phenylalanine is crystallized out from the neutralized solution and the precipitated crystals are collected by filtration. In addition, the aqueous solution containing the complex of optically active phenylalanine and optically active mandelic acid is passed through a column of a strongly acidic ion-exchange resin, the resin of the column is washed with water, the optically active phenylalanine is eluted by an aqueous ammonia solution, the eluate is then condensed to crystallize optically active phenylalanine and then, the crystals are collected by filtration.

L-isomer of phenylalanine prepared by the process of the present invention is useful as one of the components of the amino acid-infusion solution or as raw material of a synthetic sweetener.

The present invention will be concretely described more in detail while referring to the following non-limitative examples.

EXAMPLE 1

To a vessel, were added 36.46 g of DL-phenylalanine, 33.62 g of L-mandelic acid and 169.9 g of an aqueous 20% phosphoric acid solution (the total weight of 239.98 g) while stirring. The resultant mixture was heated to form a solution. After cooling the formed solution to 50° C., 0.05 g of a complex of L-phenylalanine and L-mandelic acid as a seed crystal was added to the cooled solution, and then, the solution was, cooled to 25° C. and thereafter, was stirred for 2 hours at the same temperature.

As a result, a complex of L-phenylalanine and L-mandelic acid was crystallized and the crystals were collected by filtration, were washed with 10 ml of water and then, were dried. A crude complex of L-phenylalanine and L-mandelic acid having $[\alpha]_D^{20}$ of $+56.55°$ (c=2, in H$_2$O) and an optical purity of 92.0% was obtained in yield of 26.17 g.

By recrystallizing the obtained crude crystals from 145 ml of water, 21.26 g of the purified crystals having $[\alpha]_D^{20}$ of $+55.73°$ (c=2, H$_2$O) were obtained.

After dissolving 19.04 g of the purified crystals in 76 ml of water under heating, the aqueous solution was neutralized with an aqueous 20% sodium hydroxide solution. As a result, L-phenylalanine was crystallized and the crystals were collected by filtration, were washed with 10 ml of water and were dried. L-phenylalanine having $[\alpha]_D^{20}$ of 34.02° (c=2, in H$_2$O) was obtained in yield of 7.50 g.

EXAMPLE 2

To a vessel, were added 34.24 g of DL-phenylalanine, 47.31 g of D-mandelic acid and 174.2 g of an aqueous 50% acetic acid solution (the total weight of 255.75 g) while stirring. The resultant mixture was heated to form a solution. The solution was slowly cooled to 25° C. for 3 hours and then, was stirred at the same temperature for 2 hours. As a result, a complex of D-phenylalanine and D-mandelic acid was crystallized and the crystals were collected by filtration, were washed with 10 ml of water and were dried. A crude complex of D-phenylalanine and D-mandelic acid having $[\alpha]_D^{20}$ of $-56.50°$ (c=2, in H$_2$O) and an optical purity of 91.0% was obtained in yield of 25.59 g.

By recrystallizing 24.50 g of the obtained crude crystals from 142 ml of water, 20.50 g of the purified crystals having $[\alpha]_D^{20}$ of $-55.90°$ (c=2, in H$_2$O) were obtained. After dissolving 19.04 g of the purified crystals in 950 ml of water, the solution was passed through the column of 100 ml of an ion-exchange resin (Dowex® −50W X-4, H-type). The resin in the column was washed well with water and the adsorbed material was eluted by 500 ml of an aqueous 1N ammonia solution. After condensing 1000 ml of the obtained eluate under a reduced pressure, methanol was added to the condensate to crystallize D-phenylalanine. The crystals were collected by filtration, were washed with cold water and were dried. D-phenylalanine having $[\alpha]_D^{20}$ of $-33.97°$ (c=2, in H$_2$O) was obtained in yield of 9.54 g.

EXAMPLE 3

To a vessel, were added 45.44 g of DL-phenylalanine, 50.09 g of L-mandelic acid and 152.82 g of an aqueous 80% acetic acid solution (the total weight of 248.35 g) while stirring. The resultant mixture was heated to form a solution. After cooling the formed solution to 50° C., 0.05 g of a complex of L-phenylalanine and L-mandelic acid as a seed crystal was added to the cooled solution. The mixture was cooled to 25° C. and then, was stirred for 2 hours at the same temperature.

As a result, a complex of L-phenylalanine and L-mandelic acid was crystallized. The crystals were collected by filtration, were washed with 10 ml of water and were dried. The crude complex of L-phenylalanine and L-mandelic acid having $[\alpha]_D^{20}$ of $+56.4°$ (c=2, in H$_2$O) and an optical purity of 93.6% was obtained in yield of 31.52 g.

The obtained crude complex was treated in the same manner as in Example 2 and L-phenylalanine was obtained.

EXAMPLE 4

To a vessel, were added 29.0 g of DL-phenylalanine, 32.0 g of L-mandelic acid and 113.3 g of an aqueous 80% propionic acid solution while stirring. The resultant mixture was heated to 70° C. to form a solution. The solution was cooled to 25° C. within 2.5 hours. After reheating the solution to 50° C., 0.03 g of a complex of L-phenylalanine and L-mandelic acid as a seed crystal was added thereto and the mixture was allowed to stand for 2 hours at 25° C. A complex of L-phenylalanine and L-mandelic acid was crystallized. The crystals were collected by filtration, were washed with water and were dried. The complex of L-phenylalanine and L-mandelic acid was obtained in yield of 20.2 g. After dissolving 10.0 g of the obtained crystals into 60.0 ml of water while heating, 6.0 g of an aqueous 20% sodium hydroxide solution were added to the formed solution. The resultant solution was made pH of 6.0. L-phenylalanine was crystallized. The crystals were collected by filtration, were washed with water and were dried. L-phenylalanine having $[\alpha]_D^{20}$ of $-33.1°$ (c=2, in H$_2$O) and an optical purity of 95.0% was obtained in yield of 4.0 g.

EXAMPLE 5

In 113.3 g of an aqueous 50% malonic acid solution, 38.7 g of DL-phenylalanine and 42.7 g of D-mandelic acid were dissolved at 70° C. and the resultant solution was cooled to 25° C. within 2.5 hours. After reheating the cooled solution to 50° C., 0.03 g of a complex of D-phenylalanine and D-mandelic acid was added to the reheated solution and the mixture was left to stand at 25° C. for 2 hours. A complex of D-phenylalanine and D-mandelic acid was crystallized. The crystals were collected by filtration, were washed with water and were dried. The complex was obtained in yield of 25.0 g. Thereafter, by treating the complex in the same manner as in Example 1, 10.0 g of D-phenylalanine having $[\alpha]_D^{20}$ of $+31.6°$ (c=2, in H$_2$O) and an optical purity of 91.3% was obtained.

EXAMPLE 6

In an aqueous 80% lactic acid solution, 29.0 g of DL-phenylalanine and 32.0 g of L-mandelic acid were dissolved at 70° C. and the resultant solution was cooled to 25° C. within 2.5 hours. After reheating the cooled solution to 50° C., 0.03 g of a complex of L-phenylalanine and L-mandelic acid was added to the reheated solution and the resultant mixture was left to stand at 25° C. for 2 hours. A complex of L-phenylalanine and L-mandelic acid was crystallized. The crystals were collected by filtration, were washed with water and were dried. The complex of L-phenylalanine and L-mandelic acid was obtained in yield of 19.2 g. Thereafter, by treating the complex in the same manner as in Example 1, 7.7 g of L-phenylalanine having $[\alpha]_D^{20}$ of 31 30.6° (c=2, H$_2$O) and an optical purity of 88.7% was obtained.

EXAMPLE 7

Into 113.3 g of an aqueous 30% maleic acid solution, 38.7 g of DL-phenylalanine and 42.7 g of L-mandelic acid were dissolved at 70° C. and the solution was cooled to 25° C. within 2.5 hours. After reheating the cooled solution to 42° C., 0.03 g of a complex of L-phenylalanine and L-mandelic acid was added to the reheated solution, and the resultant mixture was left to stand for 2 hours at 25° C. A complex of L-phenylalanine and L-mandelic acid was crystallized. The crystals were collected by filtration, were washed with water and were dried. The complex of L-phenylalanine and L-mandelic acid was obtained in yield of 18.8 g. Thereafter, by treating the crystals in the same manner as in Example 1, 7.5 g of L-phenylalanine having $[\alpha]_D^{20}$ of $-31.7°$ (c=2, in H$_2$O) and an optical purity of 91.6% was obtained.

EXAMPLE 8

A mixture of 33.1 g of DL-phenylalanine, 36.6 g of D-mandelic acid and 312.2 g of an aqueous 1.4% hydrochloric acid solution was heated to 75° C. to form a solution. The solution was cooled to 27° C. and then, the cooled solution was reheated to 60° C. and thereafter, 0.08 g of a complex of D-phenylalanine and D-mandelic acid was added to the reheated solution. The resultant mixture was left to stand for 2 hours at 27° C. A complex of D-phenylalanine and D-mandelic acid was crystallized. The crystals were collected by filtration, were washed with water and were dried. The complex of D-phenylalanine and D-mandelic acid was obtained in yield of 19.5 g as crystals. Thereafter, by treating the obtained crystals in the same manner as in Example 1, 7.8 g of L-phenylalanine having $[\alpha]_D^{20}$ of $-31.7°$ (c=2, in H$_2$O) and an optical purity of 91.6% was obtained.

REFERENCE EXAMPLE

Into 100 ml of water, 33.1 g of DL-phenylalanine and 73.2 g of L-mandelic acid were added and the resultant mixture was heated to a temperature of 80° to 90° C. However, since a uniform solution was not obtained, water was slowly added to the mixture. After addition of 775 ml of water, a uniform solution was obtained. Then, the solution was cooled slowly in the same manner as in Example 1 and 0.27 g of a complex of L-phenylalanine and L-mandelic acid was added to the solution during cooling. The cooling was further continued and the temperature of the mixture was made to 30° C. after 3 hours. A complex of L-phenylalanine and L-mandelic acid was crystallized. The crystals were collected by filtration, were washed with water and were dried. The complex of L-phenylalanine and L-mandelic acid was obtained in yield of 52.94 g as crystals. By treating the obtained crystals in the same manner as in Example 1, 21.2 g of L-phenylalanine having $[\alpha]_D^{20}$ of $-28.9°$ (c=2, in H$_2$O) and an optical purity of 84.10% was obtained.

What is claimed is:

1. A process for preparing optically active phenylalanine, which comprises resolving the mixture of a complex of D-phenylalanine and optically active mandelic acid and a complex of L-phenylalanine and optically active mandelic acid in a solvent containing hydrochloric acid, carboxylic acid, phosphoric acid or a salt thereof to obtain the complex having lower solubility, and removing said optically active mandelic acid from the obtained complex to obtain optically active phenylalanine.

2. The process according to claim 1, wherein the carboxylic acid is a lower fatty acid, a lower aliphatic hydroxycarboxylic acid or a lower aliphatic dicarboxylic acid.

3. The process according to claim 2, wherein the number of carbon atoms in the lower fatty acid, the lower aliphatic hydroxycarboxylic acid or the lower aliphatic dicarboxylic acid is 2 to 4.

4. The process according to claim 2, wherein the lower fatty acid is acetic acid, propionic acid, butyric acid, acrylic acid, crotonic acid or vinylacetic acid; the lower aliphatic hydroxycarboxylic acid is lactic acid; or the lower aliphatic dicarboxylic acid is oxalic acid, malonic acid or maleic acid.

5. The process according to claim 1, wherein the concentration of the carboxylic acid or salt thereof in the solvent is higher than 20 w/w % or the concentration of the phosphoric acid or salt thereof is 5 to 28 w/w % or 30 to 50 w/w %.

6. The process according to claim 5, wherein the concentration of said carboxylic acid or salt thereof is 40 to 90 w/w % or the concentration of phosphoric acid or a salt thereof is 10 to 25 w/w %.

7. The process according to claim 1, wherein the amount of hydrochloric acid used therein is 2 parts by mole or less than 2 parts by mole to one part by mole of the mixture.

8. The process according to claim 7, wherein the amount of hydrochloric acid used therein is 0.2 to 1.6 parts by mole to one part by mole of the mixture.

9. The process according to claim 1, wherein the solvent is water.

10. The process according to claim 1, wherein the resolution is carried out at a temperature of 0° to 50° C. by fractional crystallization.

* * * * *